(12) United States Patent
Van Der Wijk et al.

(10) Patent No.: US 10,488,408 B2
(45) Date of Patent: Nov. 26, 2019

(54) DETECTION OF TARGET MOLECULES IN A SAMPLE BY USING A MAGNETIC FIELD

(75) Inventors: Thea Van Der Wijk, Bunnik (NL); Eduard Gerard Marie Pelssers, Panningen (NL); Jessica Amadio, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 901 days.

(21) Appl. No.: 12/299,806

(22) PCT Filed: Apr. 27, 2007

(86) PCT No.: PCT/IB2007/051578
§ 371 (c)(1),
(2), (4) Date: Nov. 6, 2008

(87) PCT Pub. No.: WO2007/132373
PCT Pub. Date: Nov. 22, 2007

(65) Prior Publication Data
US 2009/0117670 A1    May 7, 2009

(30) Foreign Application Priority Data
May 9, 2006 (EP) .................................. 06113698

(51) Int. Cl.
*G01N 33/543* (2006.01)
*G01N 27/74* (2006.01)

(52) U.S. Cl.
CPC ..... *G01N 33/54333* (2013.01); *G01N 27/745* (2013.01); *G01N 2446/00* (2013.01)

(58) Field of Classification Search
USPC .......................... 436/526, 518, 538, 540, 164
See application file for complete search history.

(56) References Cited

U.S. PATENT DOCUMENTS 5,445,971 A * 8/1995 Rohr ............................ 436/526
5,635,364 A * 6/1997 Clark .................. B01F 11/0022
                                                                422/63
(Continued)

FOREIGN PATENT DOCUMENTS

EP          0296036 A2    12/1988
GB          2404022 A      1/2005
(Continued)

OTHER PUBLICATIONS

"Immerse." Merriam-Webster.com, retrieved from https://www.merriam-webster.com/dictionary/immerse on Apr. 20, 2017, 10 pages total.*

(Continued)

*Primary Examiner* — Christine Foster (57) ABSTRACT

The application relates to a method for detecting a target in a sample suspected of containing the target. The method comprises contacting the sample and a first binding molecule attached to a magnetic particle with a second binding molecule attached to a solid support. The first binding molecule is capable of binding to the second binding molecule, and the target is capable of interfering with this binding. Magnetic force is applied to bring the magnetic particle into close proximity with the solid support. The number of magnetic particles bound to the solid support is detected.

19 Claims, 4 Drawing Sheets

(56) References Cited

U.S. PATENT DOCUMENTS

| | | | |
|---|---|---|---|
| 5,660,990 A * | 8/1997 | Rao et al. | 435/6.11 |
| 5,981,297 A | 11/1999 | Baselt | |
| 6,342,396 B1 * | 1/2002 | Perrin | G01N 33/54306 435/7.1 |
| 6,548,311 B1 * | 4/2003 | Knoll | C12Q 1/6825 205/777.5 |
| 6,762,025 B2 * | 7/2004 | Cubicciotti | 435/6 |
| 6,897,015 B2 * | 5/2005 | Henderson et al. | 435/5 |
| 7,175,993 B2 * | 2/2007 | Salamone et al. | 435/7.93 |
| 7,611,908 B2 * | 11/2009 | Miller | B01L 3/502761 422/417 |
| 7,615,381 B2 * | 11/2009 | Masters | B01L 3/502761 422/417 |
| 2002/0045276 A1 | 4/2002 | Yguerabide | |
| 2003/0027197 A1 | 2/2003 | Nikitin | |
| 2004/0043512 A1 | 3/2004 | Song et al. | |
| 2005/0048672 A1 * | 3/2005 | Luxton et al. | 436/526 |
| 2008/0206104 A1 * | 8/2008 | Prins | G01N 27/745 422/82.01 |

FOREIGN PATENT DOCUMENTS

| | | |
|---|---|---|
| GB | 2404023 A | 1/2005 |
| WO | 93020448 A1 | 10/1993 |
| WO | 9607101 A1 | 3/1996 |
| WO | 9707243 A1 | 2/1997 |
| WO | 0114591 A1 | 3/2001 |
| WO | 03031977 A2 | 4/2003 |

OTHER PUBLICATIONS

Roger P. Ekins: Ligand assays: from electrophoresis to miniaturized microarrays, Clinical Chemistry vol. 44, No. 9, 1998, Oak Ridge Conferece, pp. 2015-2030.

Zhao, Xiaoyan et al "Competitive Immunoassay for Microliter Protein Samples with Magnetic Beads and Near-Infrared Fluorescence Detection", Anal. Chem, vol. 76, 2004, pp. 1871-1876.

* cited by examiner

DETECTION OF TARGET MOLECULES IN A SAMPLE BY USING A MAGNETIC FIELD

The invention relates to a method for detecting a target in a sample. The invention especially relates to competitive assay setups for detection of target molecules, particularly targets having a single epitope, in which the targets compete in solution with molecules attached to magnetic particles or to immobilized surfaces.

Health care research involves developing diagnostic methods to determine the presence or absence of specific compounds such as DNA, RNA, hormones, metabolites, drugs etc. Immunoassays are commonly used to determine the amount of specific proteins in body fluids to aid further diagnosis and treatment. The best-known principle of detection is a sandwich assay. Molecules of interest in a sample fluid are trapped ('sandwiched') between a biologically active sensor surface and biologically active labels (e.g. magnetic particles). Therefore, a sandwich assay requires targets with at least two epitopes. However, smaller molecules, such as drugs of abuse, generally possess only one epitope and for this reason cannot be detected by a regular sandwich assay.

A competitive or inhibition assay is the method to detect these molecules. A well-known competitive assay setup is to couple the target molecules of interest onto a surface and link antibodies to a detection tag (enzyme/fluorophore/magnetic bead). This system is used to perform a competitive assay between the target molecules in the sample and the target molecules on the surface, using the tagged antibodies (see for example GB 2404022A and GB 2404023A).

Since there is a difference in mobility of the target molecules free in solution compared to the target molecules bound to the surface or to a label, the competition is not fair and the doses response curve will not be linear. This can make it difficult to use the assay for quantitative measurements. Furthermore, the limited mobility of the targets bound to the surface or the label results in a relatively slow reaction time.

It is an object of the present invention to overcome at least one of these drawbacks.

It is a further object of the invention to provide a competitive assay for the detection of target molecules in a sample, which is suitable to be performed in a single-chamber format.

It was found that at least one of these objectives is met by the methods described in claim 1 and the claims dependent thereon.

Accordingly, in one aspect the invention relates to a method for detecting a target in a sample suspected of containing the target, comprising:
  a) contacting the sample and a first binding molecule attached to a magnetic particle, at the same time or at different times, with a second binding molecule attached to a solid support, wherein the first binding molecule is capable of binding to the second binding molecule, and wherein the target is capable of interfering with this binding; and applying a magnetic force to bring the magnetic particle into close proximity with the solid support; and
  b) detecting the number of magnetic particles bound to the solid support by virtue of the binding of the first binding molecule to the second binding molecule.

The number of particles detected in step b) of the claimed method relates to the concentration of target in the sample. A number that is reduced, e.g., reduced compared to a reference value, indicates that the sample analyzed contains target. The reference value may be a known value. Alternatively, it may be obtained in a control assay that is run simultaneously or separately using a sample that does not contain any target.

In another aspect, the invention relates to the use of a magnet for applying a magnetic force to a magnetic particle to which a first binding molecule is attached in order to bring said particle into close proximity with a solid support to which a second binding molecule is attached, wherein the first binding molecule is capable of binding to the second binding molecule, and wherein a target molecule is present which is capable of interfering with this binding.

These and other aspects of the invention will be apparent from and elucidated with reference to the embodiment(s) described hereinafter.

"Target" may be any molecule of which the concentration or presence as such is to be determined. Examples of suitable targets in the context of the present invention are molecular targets such as small molecules, drugs, proteins, enzymes, hormones, peptides and nucleic acids. Molecular targets often determine the concentration and/or presence of larger moieties, e.g. cells, viruses, or fractions of cells or viruses, tissue extract, etc.

Particularly preferred targets are those, which only have a single epitope, including single epitope small molecules, drugs, hormones, and peptides. Particularly preferred as targets are addictive drugs. An example of an addictive drug preferred as target is morphine. Other addictive drugs preferred as targets are cocaine, THC, anabolics, or drugs of the amphetamine/methamphetamine group. The target may exist as such in a sample that is analysed or may be formed in situ, e.g., during the step of contacting, for example via a reaction that takes place during that step. If a sensor is used to monitor a reaction, the target may for example be the starting product of the reaction or a reaction product.

It will be appreciated that the target to be detected according to the method of the invention will be one that interferes with the binding between the first binding molecule and the second binding molecule in a competitive manner. It will furthermore be appreciated that the first and the second binding molecule will be chosen such that the target to be detected will interfere with their binding to each other in a competitive manner. The reaction products can be detected directly by the sensing method. As well, the reaction products can be further processed prior to detection. An example of further processing is that materials are added or that the (bio)chemical or physical properties of the target are modified to facilitate detection.

As mentioned above, the method according to the invention includes a step of contacting the sample and a first binding molecule that is attached to a magnetic particle with a second binding molecule bound to a solid support. The contacting will take place in solution.

The term "in solution" as used herein means that the step, (binding) reaction or assay referred to in this context is carried out in a liquid environment. Preferably, the liquid environment is an aqueous liquid environment. The reagents that take part need not actually be dissolved in the liquid environment but may also be present in a suspended or dispersed state.

The contacting of the sample and the first binding molecule attached to the magnetic particle with the second binding molecule bound to the solid support may occur at the same time or at different times. For example, the sample may be contacted with the second binding molecule on the solid support first, and shortly thereafter the first binding molecule attached to the magnetic particle may be added. Alternatively, the first binding molecule attached to the magnetic particle may be contacted with the second binding molecule on the solid support first, and shortly thereafter the sample may be added.

In a particularly preferred embodiment of the invention, the sample and the first binding molecule attached to the magnetic particle will be contacted with the second binding molecule bound to the solid support at the same time. This can be done, e.g., in that the sample and the first binding molecule attached to the magnetic particle are mixed and subsequently contacted with the second binding molecule bound to the solid support. Alternatively, the sample and the first binding molecule attached to the magnetic particle can be added separately, but simultaneously, to the second binding molecule bound to the solid support.

The method of the invention furthermore includes applying magnetic force in step a) in order to bring the magnetic particle into close proximity with the solid support. In other words, the particles are forced onto the solid support. This step of magnetic actuation will generally lead to a reduced reaction time regarding the binding of the components participating in the competitive binding events of the assay. Furthermore, it has been surprisingly found that in certain embodiments of the invention, the sensitivity of the assay can be influenced in this way. The magnetic force during the actuation step is preferably applied in such a way so as to reduce or eliminate the impact of a difference in mobility between the target and the first binding molecule attached to the magnetic label on the binding. Thus, the magnetic force is applied to concentrate the magnetic particles to the solid support, e.g., a sensor surface, in order to compensate for the decreased mobility of the first binding molecule attached to the magnetic particle.

The magnetic force may be applied by virtue of an electromagnet. An air-cored coil or a permanent magnet are, however, also suitable.

In one embodiment of the method of the invention, the first binding molecule is capable of selectively binding both the target in the sample and the second binding molecule. The contacting step furthermore comprises allowing competition of the second binding molecule with the target for said selective binding to the first binding molecule.

Examples of suitable first binding molecules are Affibodies™, antibodies, receptor molecules, aptamers and chelators.

In cases where the target is a nucleic acid, the first binding molecule will comprise nucleic acids having a base sequence that is complementary to a part of the sequence of the target.

Particularly preferred as first binding molecules are antibodies specifically binding the target.

In case the first binding molecule is capable of selectively binding both the target in the sample and the second binding molecule, the second binding molecule is identical to the target, or is a target homologue. "Target homologue" as used herein is intended to mean either a construct which contains at least a part of the target, preferably the part that distinguishes it from other related molecules or a construct that the first binding molecule binds similarly strong to as the target. Similarly strong binding is defined as having a $K_a$ preferably a factor of $10^3$, more preferred a factor of $10^2$, most preferred a factor of 10 or smaller in difference. Without wishing to be bound by any theory it is believed that very often a target and a target homologue share the same epitopes for binding to a binding site.

In accordance with the method of the invention, the first binding molecule is attached to a magnetic particle. Suitable magnetic particles for use in the method of the invention are those which may be actuated by magnetic force. The magnetic particles may be of any shape or form. They may be magnetic, diamagnetic, paramagnetic, superparamagnetic, ferrimagnetic or ferromagnetic, i.e., any form of magnetism which generates a magnetic dipole in an electric filed, either permanently or temporarily.

In another embodiment of the method of the invention, the second binding molecule is capable of selectively binding both the target in the sample and the first binding molecule. The contacting step furthermore comprises allowing competition of the first binding molecule with the target for said selective binding to the second binding molecule.

Figure 1:
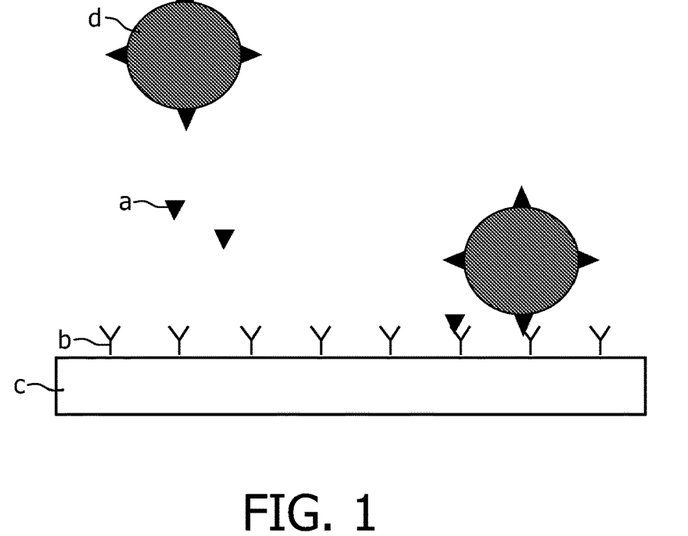
FIG. 1 shows a schematic depiction of a one-chamber competitive assay setup according to the invention wherein target molecules of interest (a) compete with target or target homologue molecules (d) attached to a magnetic particle for binding to antibodies attached to a solid support surface.

This embodiment is depicted in an exemplary manner in FIG. 1. The Figure shows a competitive assay setup, which may be used to quantitatively detect molecules with a single epitope (although molecules with two or more epitopes may also be detected). The setup does not require premixing of separate reagents, i.e., it is suitable to be operated in a single-chamber competitive assay format. This setup allows for competition of the target (a) with the first binding molecules (d) attached to magnetic particles in solution. Specifically, the target molecules (a) compete for the second binding molecules (b) on the solid support (c), e.g., a sensor surface, with target molecules or target homologues (d), which are directly or indirectly attached to the magnetic particles. The mobility difference between free target molecules (a) and the target molecules or homologues (d) bound to the magnetic particles may be overcome by application of a magnetic force (magnetic actuation). In this way, the dose response curve may surprisingly be improved towards a linear curve. This assay setup is particularly suitable for quantitative measurements of target molecules in a sample.

Examples of suitable second binding molecules are again Affibodies™, antibodies, receptor molecules, aptamers and chelators.

In the case where the target is a nucleic acid, the second binding molecule will comprise nucleic acids having a base sequence that is complementary to a part of the sequence of the target.

Particularly preferred as second binding molecules are antibodies specifically binding the target.

In case the second binding molecule is capable of selectively binding both the target in the sample and the first binding molecule, the first binding molecule is identical to the target, or is a target homologue, the term "target homologue" having the meaning as defined above.

Suitable magnetic particles for use in the methods of the present invention may have a size from about 10 nm to a few micrometers, more preferred from about 50 nm to about 1 µm. Also preferred are particles with sizes from about 100 nm to about 500 nm, e.g., particles of about 300 nm, or particles of about 200 nm. In a preferred embodiment, the magnetic particles are larger than the individual target molecules in the sample to be analyzed in the assay of the invention.

The attachment of the first binding molecule to the magnetic particle may be done via coating of the particle with the first binding molecule. It may also be done via covalent linkage, either directly or with the help of a spacer molecule. Suitable spacer molecules will be known to those skilled in the art, and include, for example, alkylene diamine or ethylene diamine.

In a preferred embodiment, the attachment is done via a strong binding couple. In this embodiment, one binding partner of a strong binding couple will be attached to the magnetic particle, and the other binding partner of the strong binding couple will be attached to the first binding molecule, or is the first binding molecule itself.

Examples of preferred strong binding couples are avidin/biotin, hapten/antibody, protein or peptide/antibody, protein/carbohydrate, protein/protein, nucleic acid/nucleic acid, protein/nucleic acids and hapten/nucleic acids.

The interaction between the protein avidin and the molecule biotin is widely applied to link biological molecules to other moieties. The affinity constant ($K_a$) of avidin with biotin is one of the highest known at approximately $10^{15}$ L/mol and thus the binding is considered irreversible under normal assay conditions. In addition to the high affinity, there are four binding sites available for biotin on each avidin molecule. The biotinylation or chemical labelling of proteins with biotin is facile and does not reduce the biological activity. Avidin can also be chemically coupled to other proteins through standard linking agents involving carbodiimide. There are a number of varieties of avidin commercially available including streptavidin and neutravidin, which differ in degree of glycosylation, isoelectric point and non-specific binding characteristics. Another alternative is the strep-tag II/strep-tactin couple.

High affinity antibodies can be raised to haptens or small molecules including dyes, drugs, hormones and vitamins. In general, antibodies to nearly any hapten can be created and a number of high affinity antibodies exist with $K_a$ greater than $10^{11}$ L/mol for molecules such as digoxigenin, 2,4-dinitrophenyl (DNP) and fluorescein-5-isothiocyanate (FITC). There are several known simple haptenylation procedures for chemically labelling molecules with haptens. Attachment of the antibodies can be accomplished also with chemical techniques similar to that described for avidin or with recombinant techniques for coupling to proteins.

The specificity and high binding affinity of proteins or peptides to their antibodies is the basis for many immunoassays. The affinity constant of such interactions can be as high as $10^{13}$ L/mol and can vary many orders of magnitude depending on the particular peptide or protein used.

Protein-protein binding occurs between specific types of proteins. For example Protein A and protein G are known for their high affinity to the Fc portion of immunoglobulins. Similarly concanavalin A is a lectin which binds to the carbohydrate fraction of glycoproteins although not as strongly as protein A and G binds to immunoglobulins. These interactions are less specific and could be used only in assays where the sample does not contain an Fc region or where the sample is not a glycoprotein. In order to achieve the desired specificity and reduce cross reactivity, antibodies and proteins within the assay for which these binding interactions are not intended may be modified. For example, one can synthesize recombinant antibodies in which the Fc or glycosylated regions are removed.

In another preferred embodiment, the attachment of the first binding molecule to the microparticle is done by coating a protein (e.g., bovine serum albumin, BSA) to which the binding molecule is linked, to the particle. For example, if the first binding molecule is morphine or a morphine homologue, or is another addictive drug, BSA is a useful protein to which these drugs can be linked. The BSA-morphine, BSA-morphine homologue or BSA-addictive drug conjugate is then coated onto the particle.

The method of the invention typically includes a washing step that is carried out prior to the detection step. During the washing step, first binding molecules which were not bound to the second binding molecule during step a) are removed. A preferred way of removing the unbound first binding molecules is by applying magnetic force, e.g., generated by an electromagnet, an air-cored coil, or a permanent magnet. Rinsing with a wash solution is, however, also possible.

As mentioned previously, the second binding molecule is attached to a solid support. In a preferred embodiment, the solid support is the surface of a sensor device. The sensor device may contain any suitable detector for detecting a label. Suitable detectors are magnetic detectors, optical detectors, sonic detectors, radioactivity detectors, or electrical detectors. The detector can be any suitable sensor to detect the presence of magnetic particles on or near to a sensor surface, based on any property of the particles, e.g. it can detect via magnetic methods (e.g. magnetoresistive, Hall, coils), optical methods (e.g. imaging, fluorescence, chemiluminescence, absorption, scattering, evanescent-field techniques, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), etc.

Particularly preferred in the context of the current invention is a magnetic detector.

The detector can be any suitable sensor based on the detection of the magnetic properties of the particle on or near to a sensor surface, e.g. a coil, a wire, magneto-resistive sensor, magneto-restrictive sensor, Hall sensor, planar Hall sensor, flux gate sensor, SQUID, magnetic resonance sensor, etc. However, the other detectors, e.g., the optical detector, are likewise preferred.

In a particularly preferred embodiment, the surface is a gold, glass or transparent plastic surface, particularly a gold, glass or transparent plastic surface coated with a protein to which the second binding molecule is bound.

Generally, the attachment of the second binding molecule to the solid support, e.g., the sensor surface, may be achieved in the ways described above as suitable in connection with the attachment of the first binding molecule to the magnetic particle. For example, it may be done via coating of the solid support with the second binding molecule. It may also be done via covalent linkage, either directly or with the help of a spacer molecule. Again, suitable spacer molecules will be known to those skilled in the art, and include, for example, alkylene diamine or ethylene diamine.

In a preferred embodiment, the attachment is done via a strong binding couple. In this embodiment, one binding partner of a strong binding couple will be attached to the solid support, and the other binding partner of the strong binding couple will be attached to the second binding molecule, or is the second binding molecule itself.

As in the case of the attachment of the first binding molecule to the magnetic particle, examples of preferred strong binding couples for attaching the second binding molecule to the solid support are avidin/biotin, hapten/antibody, protein or peptide/antibody, protein/carbohydrate, protein/protein, nucleic acid/nucleic acid, protein/nucleic acids and hapten/nucleic acids.

As also mentioned above, varieties of avidin suitable in this regard include streptavidin and neutravidin. Another alternative is the strep-tag II/strep-tactin couple.

Suitable high affinity antibodies are those raised to haptens or small molecules including dyes, drugs, hormones and vitamins. As mentioned above, such antibodies include antibodies against digoxigenin, 2,4-dinitrophenyl (DNP) and fluorescein-5-isothiocyanate (FITC).

Protein-protein binding is likewise suitable, e.g., binding of Protein A or protein G to immunoglobulins via their Fc portion. Lectins such as Concanavalin A which bind to the carbohydrate fraction of glycoproteins are likewise suitable.

In another preferred embodiment, the attachment of the second binding molecule to the solid support is done by coating a protein (e.g., bovine serum albumin, BSA) to which the binding molecule is linked, to the solid support. For example, if the second binding molecule is morphine or a morphine homologue, or is another addictive drug, BSA is a useful protein to which these drugs can be linked. The BSA-morphine, BSA-morphine homologue or BSA-addictive drug conjugate is then coated onto the solid support.

Detection of the binding reaction according to step b) of the method of the invention may be achieved in various ways. For example, the detection of the number of magnetic particles bound to the solid support by virtue of the binding of the first to the second binding molecule may be done via a magnetic sensor device.

Additionally, the sensor can be any suitable sensor to detect the presence of magnetic particles on or near to a sensor surface, based on any property of the particles, e.g. it can detect via magnetic methods (e.g. magnetoresistive, Hall, coils), optical methods (e.g. imaging, fluorescence, chemiluminescence, absorption, scattering, evanescent field techniques, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), etc. The sensor can be any suitable sensor based on the detection of the magnetic properties of the particle on or near to a sensor surface, e.g. a coil, a wire, magneto-resistive sensor, magneto-restrictive sensor, Hall sensor, planar Hall sensor, flux gate sensor, SQUID, magnetic resonance sensor, etc.

The detection can occur with or without scanning of the sensor with respect to the biosensor surface.

The sensor and methods for detection described in the present invention can be used as rapid, robust, and easy to use point-of-care biosensors for small sample volumes. The reaction chamber can be a disposable item to be used with a compact reader, containing the one or more magnetic field generating means and one or more detection means. Also, the sensor and methods for detection of the present invention can be used in automated high-throughput testing. In this case, the reaction chamber is e.g. a well plate or cuvette, fitting into an automated instrument. Measurement data can be derived as an end-point measurement, as well as by recording signals kinetically or intermittently.

The targets can be detected directly by the method for detection. As well, the particles can be further processed prior to detection. An example of further processing is that materials are added or that the (bio)chemical or physical properties of the targets are modified to facilitate detection.

Further, the assay, device, sensor an/or methods for detection of this invention are suited for sensor multiplexing (i.e. the parallel use of different sensors and sensor surfaces), label multiplexing (i.e. the parallel use of different types of labels or targets) and chamber multiplexing (i.e. the parallel use of different reaction chambers).

Alternatively, the detection of the magnetic particles which are bound to the solid support by virtue of the binding of the first to the second binding molecule may be done via binding of a third binding molecule to the first binding molecules attached to these particles, and subsequent detection of this binding. The third binding molecule is one that is capable of selectively binding to the first binding molecule. In one embodiment, first binding molecules on the magnetic particles are detected in this step which are not involved in binding to any of the second binding molecules on the solid support.

The detection of the binding of the third binding molecule to the first binding molecule in the afore-mentioned embodiment is done by virtue of a detectable label. This label may be directly linked to the third binding molecule. Alternatively, the detectable label may be attached to the third binding molecule by allowing an agent, which is linked to the detectable label and capable of selectively binding to the third binding molecule, to bind to the third binding molecule.

The labels can be detected directly by the sensing method. As well, the particles can be further processed prior to detection. An example of further processing is that materials are added or that the (bio)chemical or physical properties of the label are modified to facilitate detection. Further, the assay, device, sensor an/or method for detection of this invention are suited for label multiplexing (i.e. the parallel use of different types of labels.

Suitable labels in this regard are labels selected from the group consisting of a fluorescent label, a colorimetric label, a chemiluminescence label, an enzymatic label (e.g., horseradish peroxidase (HRP) or alkaline phosphatase (AP)), a radiolabel, an electrostatically charged label, and a donating/accepting label. A preferred label is HRP. Another preferred label is AP.

The method of the present invention is applicable to various kinds of samples. For example, it can be applied to urine samples, blood samples, sweat samples, ocular fluid samples, oral fluid (saliva) samples, or hair samples. Samples derived from the above samples by processing body fluids, tissue, or cells to bring them into a state suitable for being subjected to the assay of the invention can likewise be used. Such processing may include mixing of the samples with suitable buffers or salt solutions, chaotropic agents, detergents, or solvents, agitation, extraction via chemical or mechanical means, and the like.

In another aspect, the present invention relates to the use of a first binding molecule, a first binding molecule attached to a magnetic particle, a second binding molecule, or a second binding molecule attached to a solid support in any of the methods described and/or claimed herein, wherein the first binding molecule, the magnetic particle, the second binding molecule, and the solid support may be any of the first binding molecules, magnetic particles, second binding molecules, and solid supports as defined herein in the description and claims.

The figures and examples given below should illustrate the principles of the invention without limiting the scope of the invention.

EXAMPLE 1

Quantitation of Morphine in a Sample

A. Preparation of Magnetic Particles (MP) Attached to Anti-Morphine Antibody (Ab)

In a magnetic particle collector (MPC), MPs were collected from 100 µl of a magnetic particle solution (Ademtech, 200 nm, Protein G coated MPs, lot nr. 0433) and dissolved in 100 µl PBS+0.65% Tween 20. After addition of 10 µl monoclonal mouse antibody (1 mg/ml stock solution), the mixture was mixed for 1 h at RT, followed by washing 2 times using the MPC in 100 µl PBS+0.65% Tween 20 and once with 100 µl Triethanolamine (0.2 M, pH 8). MPs were dissolved in 1 ml DMP (20 mM) in Triethanolamine (0.2 M, pH 8) and the solution mixed for 30 min at RT. The crosslink reaction was stopped by addition of 50 µl Tris (1 M, pH 7.5, end conc.=50 mM) and mixing continued for 15 min at RT. MPs were isolated and washed 1 time using the MPC with 100 µl Tris (50 mM, pH 7.5) and 1 time with storage buffer in the MPC and finally dissolved in 100 µl of storage buffer.

B. Assay

Gold discs were etched and coated with BSA or BSA-OPI (3 µg/ml) in coating buffer (15 mM Sodium carbonate, 35 mM Sodium bicarbonate, 0.05% Sodium azide, pH to 9.6). The coated discs were washed 3 times with a wash buffer (0.05% Tween 20 in PBS). A dilution series of morphine was prepared in reaction tubes in dilution buffer (PBS+0.65% Tween 20+10 mg/ml BSA; 2× concentration to be tested). Premixed MP-solution (0.1% w/v=1 mg/ml MP in buffer) was added to each dilution in the tubes (MP-solution: morphine solution=1:1). 50 µl of each of these solutions were each put into a well and the MPs actuated via application of magnetic force for 30 sec (6-24 fN) or allowed to precipitate for 30 min. Subsequently, unbound MPs were removed by application of magnetic force (70 fN) for 30 sec and 100 µl anti-mouse IgG-HRP (1:3000 dilution of stock in dilution buffer) were added to each well, followed by incubation for 60 min at RT. Discs were washed 4 times with 200 µl wash buffer per well and transferred to white microtiter plates to wells containing wash buffer. Wash buffer was removed and 100 µl AB mix (ECL; A+B were mixed 1:1) were added and incubated for 5 min at RT. Luminescence was read.

Using this assay setup, morphine linked to BSA as a carrier was coated on a gold surface (physisorption). Anti-morphine antibodies (monoclonal) were bound to magnetic particles (MPs) coated with Protein G. Using a well plate, a dose response curve was made using free morphine to compete with the morphine on the surface for the antibody binding sites on the beads (shown here in FIG. 2). As explained above, the beads were attracted to the bio-active surface using permanent magnets below the gold surface, or allowed to precipitate onto the surface. Unbound beads were fished from the solution by putting a permanent magnet in the solution above the gold surface. To measure the amount of MPs bound to the surface, incubation with a secondary antibody (goat anti mouse antibody) linked to HRP (horseradish peroxidase) was performed and unbound secondary antibody was washed away afterwards. Then the amount of bound HRP was determined using luminol (a substrate for HRP) and luminescence measured.

Figure 2:
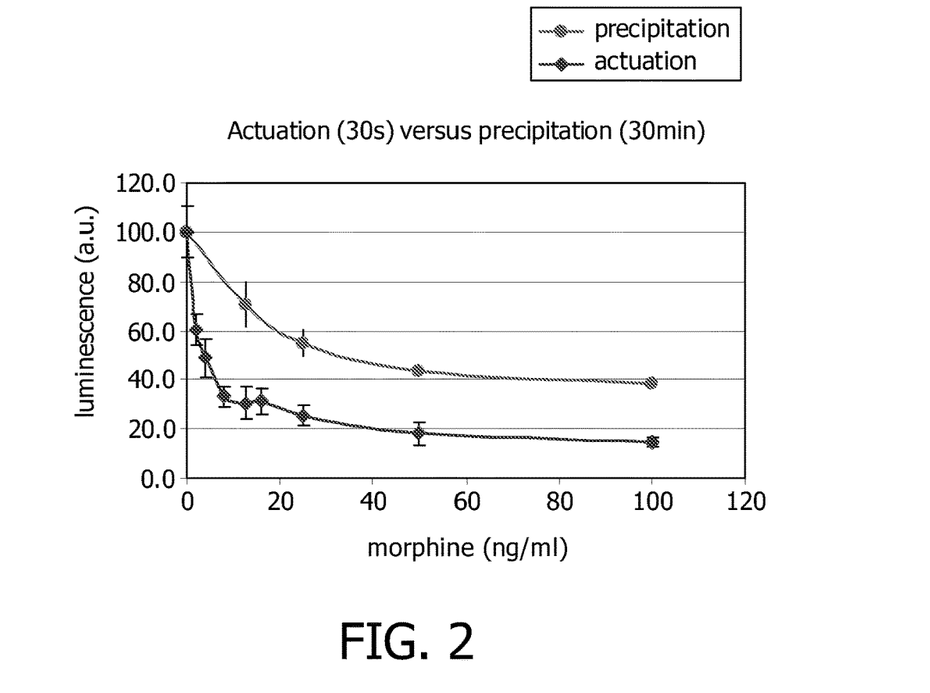
FIG. 2 shows a dose response curve of a competitive binding assay relating to morphine with and without the use of magnetic actuation to concentrate the magnetic beads coated with anti-OPI antibodies to a surface coated with BSA-OPI.

As can be seen from FIG. 2, magnetic actuation makes the dose response curve steeper, thus rendering the assay more sensitive.

EXAMPLE 2

A. Coating of Ab to a Gold Surface

Figure 3:
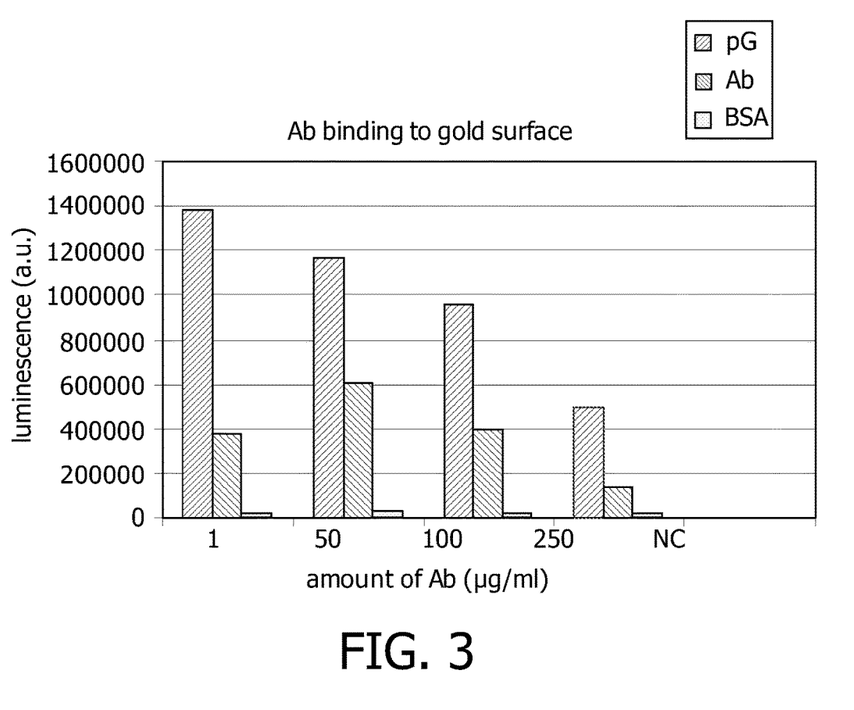
FIG. 3 shows the effectiveness of coating anti-morphine antibodies to a gold surface, detected by morphine-HRP and luminol/luminescence.

For an alternative embodiment of the method of the present invention we first needed to put Ab on a gold surface. As is shown in FIG. 3, this works best when we first put protein G (pG) on the surface. Here, we used 50 µg/ml protein G to coat the gold surface. Then we washed and incubated the surface with different amounts of Ab. After that, we incubated the surfaces with morphine-HRP, then washed. Following that, the amount of bound morphine was determined using luminol/luminescence. The signal obtained reflected the amount of functional Ab on the surface. The dark grey bar in FIG. 3 (Ab) represents Ab binding directly on the gold surface (physisorption) when leaving out protein G. The white bar represents a gold surface coated with BSA (no Ab, no protein G) to check for unspecific binding.

B. Coating of Morphine to Magnetic Particles (MPs)

Figure 4:
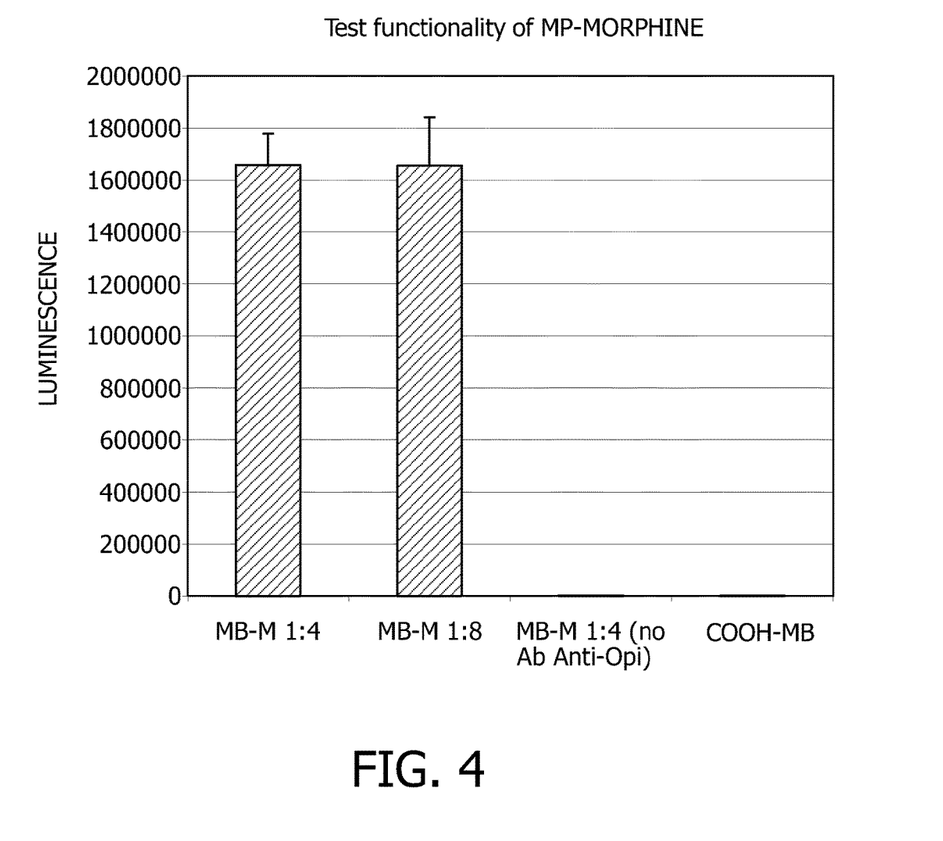
FIG. 4 shows the functionality of microparticles (MPs) to which morphine was bound, detected by binding of MP-morphine to anti-morphine Abs attached to a surface.

For this assay format we also needed morphine bound to MPs. Here we used COOH MPs purchased from Ademtech (200 nm and 300 nm beads were used). Morphine-3-glucoronide was bound to the COOH particles by first activating the COOH groups with EDC/NHS. Then the activated groups were reacted with ethylene diamine (to obtain free $NH_2$ binding sites). Morphine-3-glucoronide in turn was activated with EDC/NHC and reacted with the treated MPs. FIG. 4 shows a test for functionality of these beads. Anti-morphine Ab was put on the surface (via Protein G), as mentioned above, then beads bound to morphine were attracted to the surface using permanent magnets beneath the surface. Unbound beads were fished from the solution by putting a permanent magnet in the solution above the surface. Thereafter, incubation with biotinylated secondary Ab was performed (probably due to the high level of biotinylation, we observed that this Ab does not bind to Protein G) and after washing steps, incubation with streptavidin-HRP was done. Thereafter, luminol/luminescence was done to quantify the amount of HRP bound to the surface.

The results are shown in FIG. 4. The first two bars represent two different dilutions of the MPs, the third bar represents a parallel assay were no Ab was bound to the surface (to check for unspecific binding of MP-morphine to the surface), the fourth bar represents the same assay done in parallel with MPs that were not linked to morphine.

One advantage we observed using this assay setup is the fact that beads covered with morphine do not tend to cluster (in contrast to MPs covered with Abs, which tend to cluster). Clustering of beads is often a problem when detection of single beads is intended.

C. Competitive Assay

Figure 5:
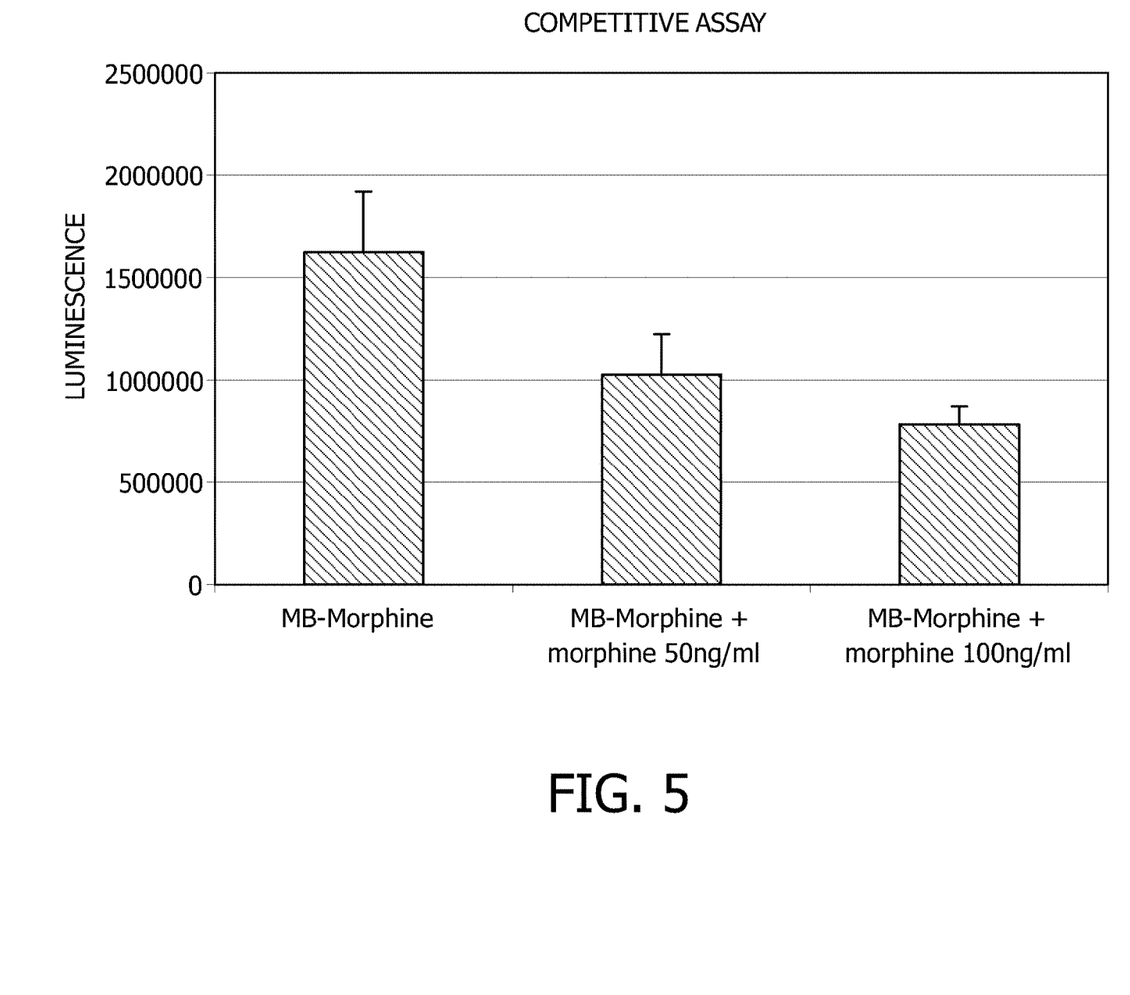
FIG. 5 shows the results of a competitive assay wherein MP-morphine binding to anti-morphine Abs attached to a surface was detected in the presence of different amounts of morphine in solution.

A competitive assay was performed in a well plate using the MPs and surfaces described above. The results are shown in FIG. 5.

The invention claimed is:

1. A method for detecting presence of target molecules in a sample, the method comprising:
   a) contacting the sample and first binding molecules attached to magnetic particles, at a same time or at different times, with second binding molecules attached to a solid support, wherein the first binding molecules are capable of binding to the second binding molecules, and wherein the target molecules are capable of interfering with the first binding molecules binding to the second binding molecules such that a portion of the first binding molecules attached to magnetic particles are not bound to the second binding molecules; and applying a magnetic force to bring the magnetic particles into close proximity with the solid support; and b) determining magnetic particles bound to the solid support by virtue of the binding of the first binding molecules attached to magnetic particles to the second binding molecules, wherein the determining of the bound magnetic particles comprises removing the portion of the first binding molecules attached to magnetic particles that are not bound to the second binding molecules, and allowing third binding molecules, which are capable of selectively binding to the first binding molecules, to bind to the first binding molecules that are bound to the second binding molecules, and detecting the binding of the third binding molecules to the first binding molecules.

2. The method of claim 1, wherein the first binding molecules are capable of selectively binding to the target molecules in the sample and the second binding molecules, and wherein the contacting of the sample and the first binding molecules enables competition of the second binding molecules with the target molecules for said selective binding to the first binding molecule.

3. The method of claim 2, wherein the second binding molecules are identical to the target, or are target homologues.

4. The method of claim 1, wherein the second binding molecules are capable of selectively binding the target molecules in the sample and the first binding molecules, and wherein the contacting of the sample and the first binding molecules enables competition of the first binding molecules with the target molecules for said selective binding to the second binding molecules.

5. The method of claim 4, wherein the first binding molecules are identical to the target molecules, or are target homologues.

6. The method of claim 1, wherein the target molecules are selected from the group consisting of a small molecule, a drug, a protein, a peptide, an enzyme, a hormone and a nucleic acid.

7. The method of claim 1, wherein the target molecules comprise an addictive drug, selected from the group consisting essentially of morphine, cocaine, tetrahydrocannabinol (THC), anabolics, or a drug of an amphetamine/methamphetamine group.

8. The method of claim 1, wherein the magnetic force is applied in such a way so as to reduce or eliminate an impact of a difference in mobility between the target molecules and the first binding molecules attached to magnetic particles with regard to binding to the second binding molecules.

9. The method of claim 8, wherein the magnetic force is applied using an electromagnet, an air-cored coil, or a permanent magnet.

10. The method of claim 1, wherein the first binding molecules are respectively attached to said magnetic particles via spacer molecules, proteins or strong binding couples.

11. The method of claim 10, wherein the spacer molecules comprise alkylene diamine or ethylene diamine.

12. The method of claim 1, wherein the solid support is a surface of a sensor device.

13. The method of claim 12, wherein the surface of the sensor device is a gold surface.

14. The method of claim 13, wherein the gold surface is coated with a protein to which the second binding molecules are bound.

15. The method of claim 1, wherein said sample consists of, or is derived from, urine, blood, sweat, ocular fluid, saliva, or hair.

16. The method of claim 1, wherein the magnetic particles are selected from the group consisting essentially of magnetic, diamagnetic, paramagnetic, superparamagnetic, ferrimagnetic, and ferromagnetic particles.

17. The method of claim 1, wherein each of the magnetic particles has a size from about 10 nm to about 10 µm.

18. The method of claim 1, wherein each of the magnetic particles has a size from about 50 nm to about 1 µm.

19. The method of claim 1, wherein each of the magnetic particles has a size from about 100 nm to about 500 nm.

* * * * *